(12) United States Patent
Wiedemann et al.

(10) Patent No.: US 11,796,456 B2
(45) Date of Patent: Oct. 24, 2023

(54) MEASURING DEVICE FOR ANALYZING THE COMPOSITION OF A FUEL GAS, HAVING A FILTER CHAMBER ARRANGED UPSTREAM OF A DETECTOR

(71) Applicant: ABB Schweiz AG, Baden (CH)

(72) Inventors: Susanne Wiedemann, Brachttal (DE); Wolfgang Kleemann, Oberursel (DE); Carsten Rathke, Hanau (DE); Matias-Hugo Clavin, Lanus Oeste (AR); Juergen Kappler, Frankfurt am Main (DE)

(73) Assignee: ABB Schweiz AG, Baden (CH)

( * ) Notice: Subject to any disclaimer, the term of this patent is extended or adjusted under 35 U.S.C. 154(b) by 126 days.

(21) Appl. No.: 17/078,104

(22) Filed: Oct. 23, 2020

(65) Prior Publication Data

US 2021/0041354 A1     Feb. 11, 2021

Related U.S. Application Data

(63) Continuation of application No. PCT/EP2019/060022, filed on Apr. 17, 2019.

(30) Foreign Application Priority Data

Apr. 25, 2018   (EP) ..................... 18169319

(51) Int. Cl.
*G01N 21/3504* (2014.01)
*G01N 21/17* (2006.01)
(Continued)

(52) U.S. Cl.
CPC ..... *G01N 21/3504* (2013.01); *G01N 21/1702* (2013.01); *G01N 33/0006* (2013.01);
(Continued)

(58) Field of Classification Search
None
See application file for complete search history.

(56) References Cited

U.S. PATENT DOCUMENTS

| | | | | |
|---|---|---|---|---|
| 4,027,972 A | * | 6/1977 | Davies | G01N 21/3518 250/343 |
| 4,058,725 A | * | 11/1977 | Aine | G01N 21/1702 250/343 |
| 4,700,073 A | * | 10/1987 | Fabinski | G01N 21/3504 250/343 |
| 5,077,469 A | | 12/1991 | Fabinski et al. | |

(Continued)

FOREIGN PATENT DOCUMENTS

| | | |
|---|---|---|
| CH | 685889 A5 | 10/1995 |
| DE | 3522949 A1 | 1/1987 |

(Continued)

OTHER PUBLICATIONS

Kovalyov, A. et al., "Resonant optoacoustic detector in nondispersive gas analyzer scheme" Infrared Physics & Technology 38 (1997) 415-421.*

*Primary Examiner* — Edwin C Gunberg
(74) *Attorney, Agent, or Firm* — Leydig, Voit & Mayer, Ltd.

(57) ABSTRACT

A measuring device for analyzing a composition of a fuel gas including at least a first gas and a second gas different from the first gas, the first gas and the second gas absorbing an infrared light in at least one common first wavelength range in the electromagnetic spectrum, the measuring device including: an intermittent first infrared emitter; a first sample chamber for receiving the fuel gas; a first detector including at least the first gas and operating according to a photoacoustic effect; and a first filter chamber containing the second gas. The first sample chamber, the first detector, and the first filter chamber are arranged relative to each other such that an infrared light emitted from the first infrared (Continued)

emitter passes through the first sample chamber and the first filter chamber and impinges on the first detector.

14 Claims, 4 Drawing Sheets

(51) Int. Cl.
  *G01N 33/00* (2006.01)
  *G01N 33/22* (2006.01)
(52) U.S. Cl.
  CPC ... *G01N 33/225* (2013.01); *G01N 2021/1704* (2013.01); *G01N 2201/06113* (2013.01); *G01N 2201/127* (2013.01)

(56) References Cited

U.S. PATENT DOCUMENTS

| | | | |
|---|---|---|---|
| 5,292,666 A | 3/1994 | Fabinski et al. | |
| 6,006,585 A | 12/1999 | Forster | |
| 2011/0062056 A1* | 3/2011 | Tate | C10G 9/206 |
| | | | 208/106 |
| 2011/0098936 A1* | 4/2011 | Bats | G01N 9/36 |
| | | | 702/24 |

FOREIGN PATENT DOCUMENTS

| | | | | |
|---|---|---|---|---|
| EP | 0072222 A1 | 2/1983 | | |
| EP | 0685728 A1 | 12/1995 | | |
| EP | 1936355 A1 * | 6/2008 | ......... | G01N 21/1702 |
| GB | 2113833 A | 8/1983 | | |
| JP | 60-149949 A | 8/1985 | | |
| WO | WO 2010/145809 A1 | 12/2010 | | |

\* cited by examiner

US 11,796,456 B2

MEASURING DEVICE FOR ANALYZING THE COMPOSITION OF A FUEL GAS, HAVING A FILTER CHAMBER ARRANGED UPSTREAM OF A DETECTOR

CROSS-REFERENCE TO PRIOR APPLICATION

This application is a continuation of International Patent Application No. PCT/EP2019/060022, filed on Apr. 17, 2019, which claims priority to European Patent Application No. EP 18169319.3, filed on Apr. 25, 2018. The entire disclosure of both applications is hereby incorporated by reference herein.

FIELD

The invention relates to a measuring device for analysing a composition of a fuel gas comprising at least a first gas and a second gas different from the first, the first gas and the second gas being capable of absorbing infrared light in at least one common first wavelength range in the electromagnetic spectrum.

BACKGROUND

Such known measuring devices often have an intermittent first infrared emitter, a first sample chamber for receiving the fuel gas, a first detector containing at least the first gas and operating according to the photoacoustic effect. Since the first gas and the second gas absorb infrared light in the first wavelength range, the first detector has a cross-sensitivity to the second gas. This cross-sensitivity can lead to inaccurate measurement of a concentration of the first gas in the fuel gas using the first detector.

SUMMARY

In an embodiment, the present invention provides a measuring device for analyzing a composition of a fuel gas comprising at least a first gas and a second gas different from the first gas, wherein the first gas and the second gas absorb an infrared light in at least one common first wavelength range in the electromagnetic spectrum, the measuring device comprising: an intermittent first infrared emitter; a first sample chamber configured to receive the fuel gas; a first detector comprising at least the first gas and operating according to a photoacoustic effect; and a first filter chamber containing the second gas, wherein the first sample chamber, the first detector, and the first filter chamber are arranged relative to each other such that an infrared light emitted from the first infrared emitter passes through the first sample chamber and the first filter chamber and impinges on the first detector.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
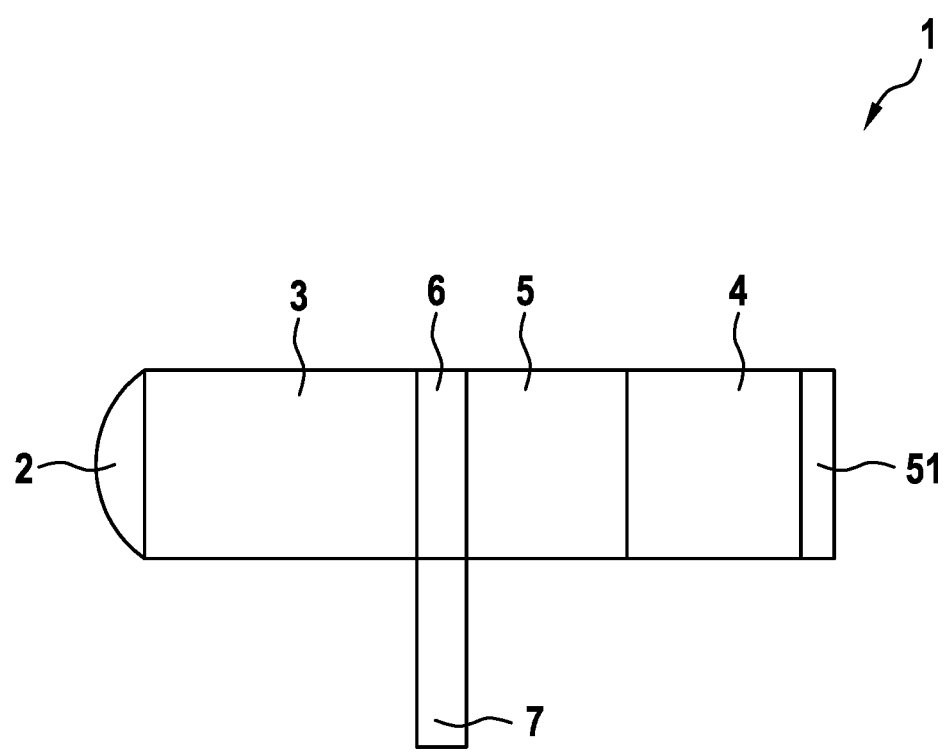
FIG. 1 shows a measuring device for analysing a composition of a fuel gas by means of a first filter chamber.

In an embodiment, the present invention further improves a measuring device of the generic type in such a way that cross-sensitivity of the first detector is reduced.

In embodiments, the present invention provides a measuring device with the technical features described herein and a method with the technical features described herein. Advantageous embodiments of the measuring device and further favourable features of the method are described herein.

To solve the technical problem, a measuring device is used to analyse a composition of a fuel gas comprising at least a first gas and a second gas different from the first, the first gas and the second gas being capable of absorbing infrared light in at least one common first wavelength range in the electromagnetic spectrum. The measuring device comprises at least one intermittent first infrared emitter, a first sample chamber for receiving the fuel gas, a first detector containing at least the first gas and operating according to the photoacoustic effect. The proposed measuring device is characterized in that the measuring device comprises a first filter chamber containing the second gas, and the first sample chamber, the first detector and the first filter chamber are arranged relative to each other in such a way that an infrared light emitted by the first infrared radiator can pass through the first sample chamber and the first filter chamber and strike the first detector.

Composition analysis is primarily a determination of mass and/or substance quantity ratios between the first and second gas and preferably other gases contained in the fuel gas. The fuel gas is preferably natural gas containing various hydrocarbon compounds. Thus the fuel gas contains at least the first gas, which is preferably propane ($C_3H_8$), and the second gas, which is preferably methane ($CH_4$). The first wavelength range can be defined by a lower and an upper limit, where the two limits can be described by a value of a wave number, for example 2750 l/cm for the lower limit and 2900 l/cm for the upper limit.

The intermittent first infrared radiator can, in a first variant, have an infrared light source and a mechanical pulse shaper arranged in the beam path of the infrared light source. In a second variant, the first infrared radiator can be designed in the form of a pulsed laser. In any case, the infrared radiator generates an infrared radiation which has an intensity which varies over a time interval. The intensity preferably changes in pulses from a first low level to a second higher level. The infrared radiator emits the infrared radiation in a main direction, which points from the infrared radiator towards the first detector.

The variable intensity causes the first gas in the first detector to absorb a varying amount of energy from the infrared radiation over the time interval.

As a result, a quantity of heat is generated in the first detector that changes over the time interval, resulting in a pressure that changes over time. This pressure, which changes over time, generates pressure waves, which the first detector picks up and which are amplified by an amplifier of the measuring device and processed into signals. The signals can be evaluated with the aid of an evaluation unit in such a way that a relationship can be determined between a difference in an amplitude of the pressure wave or signal which varies over time and a first concentration of the first gas in the first sample chamber. The effect that a pressure wave can be generated by absorption of electromagnetic radiation is called photoacoustic effect.

Because the measuring device comprises the first filter chamber with the second gas, the second gas absorbs those electromagnetic waves of infrared radiation which have an energy that an electron of an atom of a molecule of the second gas absorbs when it is transferred from a ground state to an excited state. The energy absorbed by the electron depends, among other things, on a rotation and oscillation of the molecules of the second gas. In contrast to sharply defined energy values for atoms, many absorbable energy values are close together in molecules and form wider dark areas, so-called absorption bands, in the absorption spectrum. The first and the second gas now have overlapping absorption bands.

After the electrons have absorbed the energy, the electrons release the absorbed energy. This can take place in the form of heat or electromagnetic radiation, for example. The important thing is that the energy emitted by the electrons is distributed in all directions in space, thus weakening an intensity of those electromagnetic waves that have the respective absorbed energies of the electrons of the second gas in the direction of the main direction. As a result, these electromagnetic waves can hardly be detected in the first detector.

The concentration of the second gas in the first filter chamber is preferably constant for different fuel gases with which the first sample chamber is filled. Thus the above described weakening of the intensity in the main direction is largely independent of a concentration of the second gas in the fuel gas. With the proposed measuring device, the above-described attenuation is mainly caused by the second gas in the first filter chamber and not by the second gas in the first sample chamber. Furthermore, the attenuation is also performed for an intensity of those waves which lie within the first wavelength range, i.e. which correspond to the overlapping absorption bands. For this reason, a cross-sensitivity of the first detector to the second gas can be reduced with the proposed measuring device.

This not only allows a pressure wave detected by the first detector to calculate a concentration of the first gas in the fuel gas to be distorted in relation to a concentration of the second gas in the fuel gas. Furthermore, a sensitivity of the first detector to that electromagnetic radiation can be increased which preferably corresponds to a corrected absorption spectrum of the first gas. The corrected absorption spectrum preferably does not contain the overlapping absorption bands. This is due to the fact that any total electromagnetic energy incident on the first detector is reduced by the first filter chamber located before the first detector. Thus, an amplifier connected to the first detector can be operated with a lower series resistance compared to a measuring device that does not have the first filter chamber. The series resistor can be adjusted by adjusting a potentiometer. Due to the increased sensitivity, the amplitude of the difference in the signal can be increased, which allows more accurate detection of concentration differences of the second gas in the fuel gas.

An advantageous embodiment provides that the measuring device has a first calibration chamber for calibrating the measuring device. The first calibration chamber contains a mixed gas with a predetermined quantitative ratio between a first quantity of the first gas and a second quantity of the second gas and is positionable between the first sample chamber and the first filter chamber.

The predetermined quantity ratio is preferably in a range where there is a quantity ratio between the quantity of the first gas and the quantity of the second gas in the fuel gas. The range may, for example, be defined by a lower and an upper limit value, which may be prescribed by safety regulations. Preferably, the calibration chamber shall be movable in the measuring device. The purpose of this is that the calibration chamber can be moved between the infrared emitter and the first detector to a first position when there is no fuel gas in the first sample chamber. In such a state of the measuring device the amplifier can be adjusted in such a way that with the aid of the first detector an absorption of electromagnetic waves which lie within the corrected absorption spectrum can be detected with the greatest possible sensitivity of a total unit formed by the first detector and the amplifier.

Preferably, the measuring device comprises an additional chamber which is mechanically fixed to the calibration chamber. This has the advantage that the additional chamber can be moved between the first infrared emitter and the first detector when the first calibration chamber leaves the first position. The further chamber preferably contains nitrogen.

In a preferred embodiment, the first filter chamber is designed as a second detector which operates according to the photoacoustic effect. This has the advantage that the first filter chamber not only reduces the cross-sensitivity of the first detector, but that the first filter chamber can also be used to determine a concentration of the second gas in the fuel gas. The second detector preferably works on the same principle as the first detector, with the difference that the second detector contains the second gas instead of the first gas.

In a further preferred embodiment, the first sample chamber has a fluid inlet and a fluid outlet, whereby the measuring device can be operated while the fuel gas is flowing through the first sample chamber. The fact that the measuring device can be operated while the fuel gas is flowing through the first sample chamber allows the first sample chamber to be placed in an access line for the fuel gas to a burner or in a branch of such an access line. This allows a permanent measurement of the composition of the fuel gas, whereby the burner can be controlled as a function of the recorded composition of the fuel gas with the aid of the proposed measuring device. This enables an optimized combustion in the burner and also makes an exact calculation of the costs of the fuel gas possible.

In a further development of the invention, it is provided that the fuel gas comprises at least a third gas and a fourth gas different from the third, the third gas and the fourth gas being capable of absorbing infrared light in at least one common second wavelength range in the electromagnetic spectrum. According to this further training, the measuring device comprises an intermittent second infrared emitter, a second sample chamber for receiving the fuel gas, a third detector containing at least the third gas and operating according to the photoacoustic effect, and a second filter chamber containing the fourth gas. The second sample chamber, the third detector and the second filter chamber are arranged relative to each other in such a way that an infrared light emitted from the second infrared radiator can pass through the second sample chamber and the second filter chamber and strike the third detector and the fuel gas can be directed from the fluid outlet of the first sample chamber to a fluid inlet of the second sample chamber.

This further training of the measuring device has the advantage that proportions, in particular mass or substance fractions, of the first and third gas in the fuel gas can be determined. The third gas is preferably ethane and the fourth gas preferably propane.

In a further optional configuration, it is provided that the measuring device has a fourth detector, which is arranged between the second infrared radiator and the third detector and has a fifth gas. With this configuration, a combined measurement of a concentration of the third and fifth gas can be carried out, whereby the cross-sensitivity of the third detector to the fourth gas is additionally reduced. The fifth gas is preferably carbon dioxide.

In order to solve the aforementioned technical problem, a method for the analysis of a fuel gas with the aid of a measuring device according to one of the above-described designs is also proposed. The procedure has the following steps. In a first step the fuel gas is introduced into the first sample chamber. In a second step an intermittent infrared radiation is generated with the first infrared radiator. In a third step, a first intensity of infrared radiation is detected with the first detector. In a fourth step, at least one concentration of the first gas is determined as a function of the first intensity of the infrared radiation.

The method may advantageously include the following further steps. In a sixth step, a second intensity of infrared radiation can be detected with the second detector. In a seventh step, a second concentration of the second gas can be determined as a function of the second intensity of the infrared radiation. The numbering of the individual steps does not indicate a necessary sequence of the method. So it is possible to determine the second concentration before the first concentration.

Within the scope of the further training of the measuring devices described above, it is just as well possible that the method is supplemented by the following further steps. Thus, in an eighth step, the fuel gas can be conducted from the first sample chamber to the second sample chamber and in a ninth step, intermittent infrared radiation can be generated with the second infrared radiator. A tenth step may provide for the detection of a third intensity of infrared radiation with the third detector. In an eleventh step, a third concentration of the third gas is preferably determined as a function of the third intensity of the infrared radiation. Preferably, in a twelfth step, a fourth intensity of the infrared radiation is detected with the second filter chamber, whereby the second filter chamber is designed as a fourth detector. A thirteenth step may provide for the detection of a fourth concentration of the fourth gas as a function of the fourth intensity of the infrared radiation.

Depending on the first, second, third and/or fourth concentration, preferably a calorific value, a heating value, a lower Wobbe index and/or an upper Wobbe index of the fuel gas is determined.

FIG. 1 shows a measuring device 1 for analysing a composition of a fuel gas comprising at least a first gas, preferably propane, and a second gas different from the first, preferably methane. The first and the second gas can absorb infrared light in at least one common first wavelength range in the electromagnetic spectrum. The measuring device 1 further comprises an intermittent first infrared radiator 2, a first sample chamber 3 for receiving the fuel gas, a first detector 4 and a first filter chamber 5. The first detector 4 comprises at least the first gas and operates according to the photoacoustic effect. The first filter chamber 5 contains the second gas and is located between the first detector 4 and the first infrared radiator 2. This allows an infrared light emitted by the first infrared radiator 2 to pass first through the first sample chamber 3, then through the first filter chamber 5 and then to hit the first detector 4.

The measuring device 1 shown in FIG. 1 shows a special design of the proposed measuring device, in which measuring device 1 additionally has a calibration chamber 6. The calibration chamber 6 is displaceably arranged between the first sample chamber 3 and the first filter chamber 5. The calibration chamber 6 can be shifted in such a way that it is arranged between the first sample chamber 3 and the first filter chamber 5 in a first position as shown in FIG. 1. In addition, calibration chamber 6 can be moved in such a way that it is located in a second position not shown in FIG. 1, in which a mixed gas contained in calibration chamber 6 is not hit by an infrared beam emitted from the first infrared radiator 2 towards the first detector 4. The mixed gas has a predetermined quantity ratio between a first quantity of the first gas and a second quantity of the second gas.

An empty chamber 7 is preferably located between the first sample chamber 3 and the first filter chamber 5 when the calibration chamber 6 is in the second position. The empty chamber 7 preferably contains nitrogen. A special design of the measuring device 1 provides that the first filter chamber 5 is designed in the form of a second detector which operates according to the photoacoustic effect and with which a concentration of the second gas in the fuel gas can be determined. The second detector is preferably similar to the first detector described above, the second detector having the second gas instead of the first gas.

Figure 2:
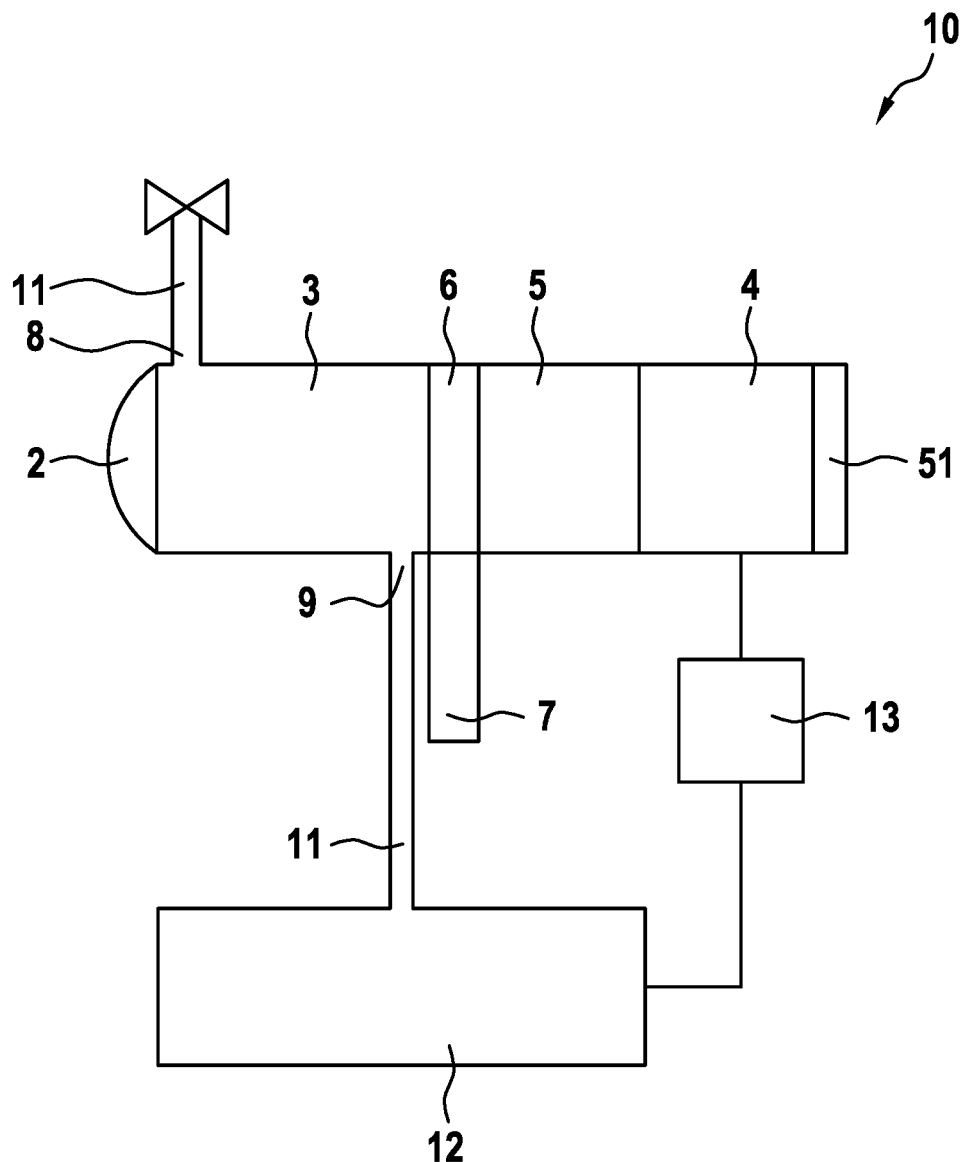
FIG. 2 shows a further measuring device for analysing a composition of a fuel gas by means of a first filter chamber.

FIG. 2 shows another measuring device 10, which has the same components as measuring device 1 shown in FIG. 1. In addition, the first sample chamber 3 has a fluid inlet 8 and a fluid outlet 9, allowing the measuring device to be operated while the fuel gas is flowing through the first sample chamber 3.

FIG. 2 also shows a possibility in which the first sample chamber 3 is connected to an inlet 11 for the fuel gas of a burner 12 so that the fuel gas for burner 12 flows through sample chamber 3. Thus, the fuel gas led through the inlet 11 to the burner 12 can be permanently analyzed by means of the measuring device 10. The analysis comprises in an advantageous manner a determination of a lower and/or upper calorific value and a lower and/or upper Wobbe index, these values preferably being calculated with the aid of an evaluation unit 13. These calculated values can be used to control the burner 12. For this purpose, the evaluation unit 13 sends the calculated values to a control unit of the burner 12. Furthermore, these values can also be used to calculate a price of the fuel gas.

Figure 3:
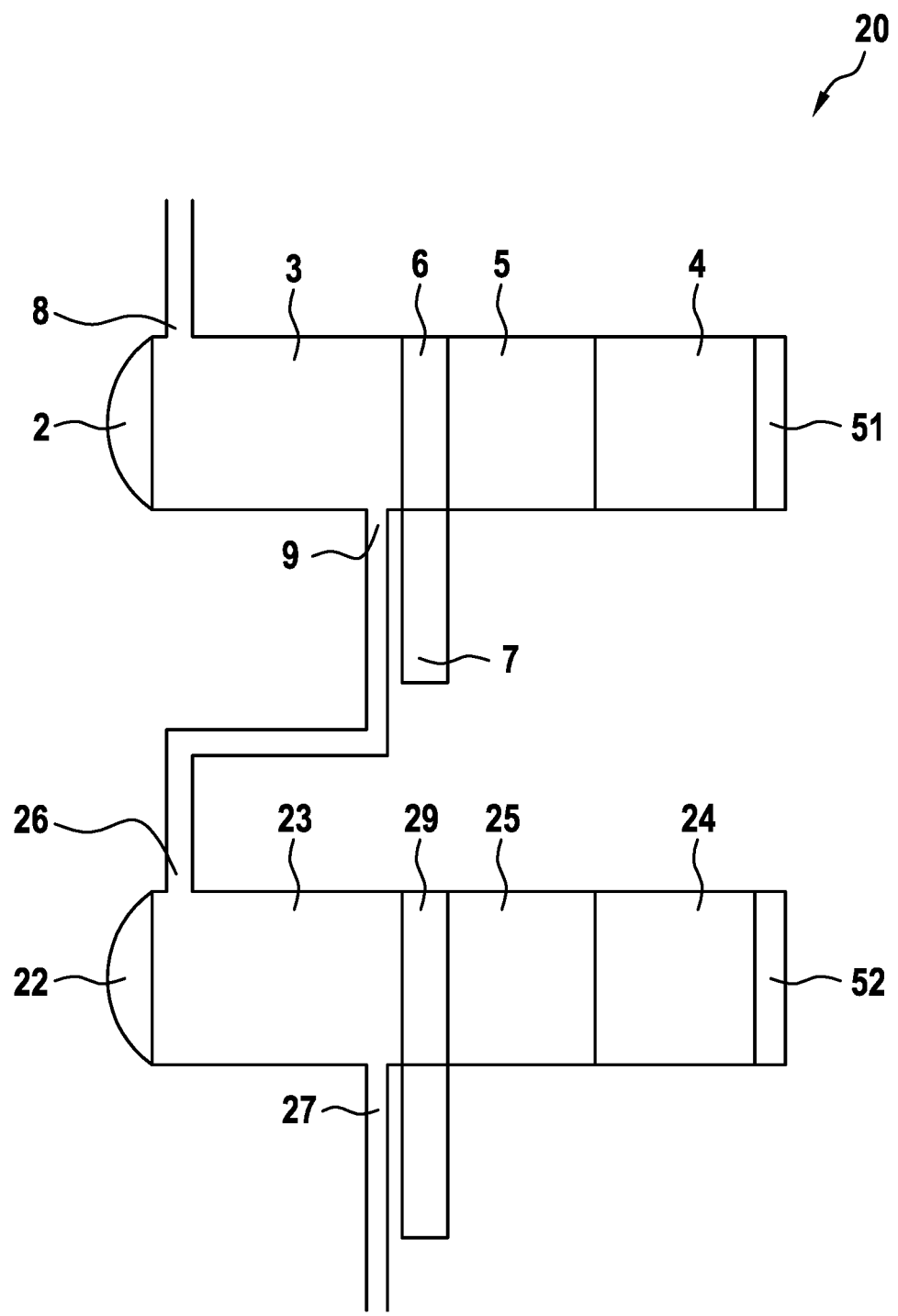
FIG. 3 shows a further measuring device for analysing a composition of a fuel gas by means of two filter chambers.

FIG. 3 shows another measuring device 20, which has the same components as measuring device 10 shown in FIG. 2. In addition, the measuring device 20 has an intermittent second infrared radiator 22, a second sample chamber 23 for receiving the fuel gas, a third detector 24, which has at least a third gas, preferably ethane, and operates according to the photoacoustic effect, and a second filter chamber 25, which contains propane in fourth gas, preferably propane. The second sample chamber 23, the third detector 24 and the second filter chamber 25 are arranged relative to each other in such a way that an infrared light emitted by the second infrared radiator 22 can pass through the second sample chamber 23 and the second filter chamber 25 and strike the third detector 24. Furthermore, the fuel gas can be conducted from the fluid outlet 9 of the first sample chamber 3 to a fluid inlet 26 of the second sample chamber 23. The fuel gas can leave the second sample chamber 23 via a fluid outlet 27 of the second sample chamber. FIG. 3 represents a variant in which the measuring device 20 has a second calibration chamber 29, which is located between the second sample chamber 23 and the second filter chamber 25. The second calibration chamber 29 preferably contains a mixed gas comprising the third and the fourth gas, wherein a mixing ratio between the third and the fourth gas is known.

Figure 4:
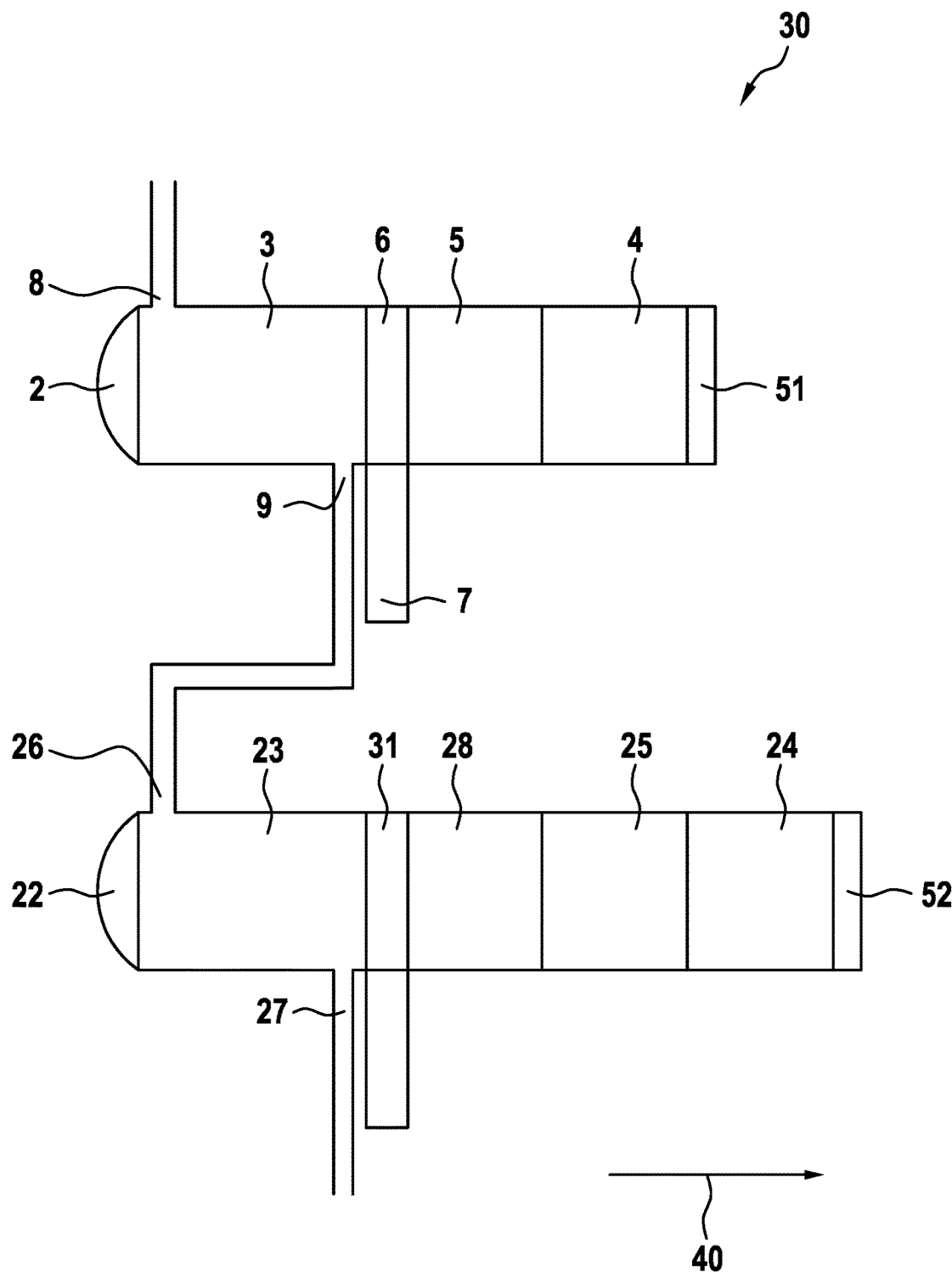
FIG. 4 shows a further measuring device for analysing a composition of a fuel gas by means of two filter chambers and four detectors.

FIG. 4 shows another measuring device 30, which has the same components as measuring device 20 shown in FIG. 3. In addition, the measuring device 20 has a fourth detector 28, which is located between the second infrared radiator 22 and the third detector 24 and has a fifth gas, preferably carbon dioxide. By means of the fourth detector, a concentration of the fifth gas in the fuel gas can be detected. Furthermore, FIG. 4 shows a special design of the measuring device 30, in which the measuring device 30 has a second calibration chamber 31, which is located between the second sample chamber 23 and the fourth detector 28. The second calibration chamber 31 preferably contains a mixed gas comprising the third and the fifth gas, wherein a mixing ratio between the third and the fifth gas is known.

Calibration chambers 6, 29 and 31 function in the same way as the first calibration chamber described above, except that the respective calibration chambers 6, 29 and 31 are filled with different gases.

All boundaries of all chambers shown in FIGS. 1 to 4 are transparent in a horizontal direction 40 to the infrared radiation emitted by the first or second radiator. The measuring devices block the infrared radiation in direction 40 at their respective ends by means of a cover plate 51, 52.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS 1, 10, 20, 30 Measuring device
2, 22 Infrared emitters
3, 23 Sample chamber
4, 24, 28 Detector
5, 25 Filter chamber
6, 29, 31 Calibration chamber
7 Empty chamber
8, 26 Fluid inlet
9, 27 Fluid outlet
11 Inflow
12 Burners
13 Evaluation unit
40 horizontal direction
51, 52 Cover lens

What is claimed is:

1. A measuring device for analyzing a composition of a fuel gas comprising at least a first gas and a second gas different from the first gas, wherein the first gas and the second gas absorb an infrared light in at least one common first wavelength range in the electromagnetic spectrum, the measuring device comprising:
   an intermittent first infrared emitter;
   a first sample chamber configured to receive the fuel gas;
   a first detector comprising at least the first gas and operating according to a photoacoustic effect;
   a first filter chamber containing the second gas; and
   a first calibration chamber configured to calibrate the measuring device, the first calibration chamber containing a mixed gas with a predetermined quantity ratio between a first quantity of the first gas and a second quantity of the second gas, and being positionable between the first sample chamber and the first filter chamber,
   wherein the first calibration chamber is arranged movably in the measuring device, and wherein the first sample chamber, the first detector, and the first filter chamber are arranged relative to each other such that an infrared light emitted from the first infrared emitter passes through the first sample chamber and the first filter chamber, and impinges on the first detector,
   wherein the first sample chamber has a fluid inlet and a fluid outlet and the measuring device is operable during a flow of the fuel gas through the first sample chamber, and the first sample chamber is connected to a fuel gas inlet for a burner so that the fuel gas for the burner flows through the first sample chamber, and
   wherein an evaluation unit is provided, via which a calculated value for controlling the burner can be transmitted to a control unit of the burner.

2. The measuring device according to claim 1, wherein the first filter chamber is configured as a second detector which operates according to the photoacoustic effect.

3. The measuring device according to claim 1, wherein the fuel gas comprises at least a third gas and a fourth gas different from the third,
   wherein third gas and the fourth gas absorb infrared light in at least one common second wavelength range in the electromagnetic spectrum,
   wherein the measuring device further comprises an intermittent second infrared emitter, a second sample chamber configured to receive the fuel gas, a third detector comprising at least the third gas and operating by the photoacoustic effect, and a second filter chamber containing the fourth gas,
   wherein the second sample chamber, the third detector, and the second filter chamber are arranged relative to one another such that an infrared light emitted by the second infrared emitter passes through the second sample chamber and the second filter chamber and impinges on the third detector, and wherein the fuel gas is conductible from the fluid outlet of the first sample chamber to a fluid inlet of the second sample chamber.

4. The measuring device according to claim 3, further comprising a fourth detector arranged between the second infrared emitter and the third detector and comprising a fifth gas.

5. The measuring device according to claim 4, wherein the first gas is propane and the second gas is methane.

6. The measuring device according to claim 5, wherein the third gas is ethane and the fourth gas is propane.

7. The measuring device according to claim 6, wherein the fifth gas is carbon dioxide.

8. A method for analyzing a fuel gas by the measuring device according to claim 1, wherein the measuring device further comprises a first calibration chamber configured to calibrate the measuring device, the first calibration chamber being positionable between the first sample chamber and the first filter chamber and arranged movably in the measuring device, the method comprising the following steps:
   feeding the fuel gas into the first sample chamber;
   generating an intermittent infrared radiation with the first infrared emitter;
   detecting a first intensity of infrared radiation with the first detector;
   determining at least one concentration of the first gas as a function of a first intensity of the infrared radiation; and
   transmitting the calculated values to a control unit of a burner for controlling the burner.

9. The method according to claim 8, the first calibration chamber contains a mixed gas with a predetermined quantity ratio between a first quantity of the first gas and a second quantity of the second, and
   wherein the method comprises the following additional steps:
   detecting a second intensity of infrared radiation with the second detector, and
   determining at least a second concentration of the second gas depending on the second intensity of the infrared radiation.

10. The method according to claim 9 comprising the following additional steps:
   introducing the fuel gas from the first sample chamber into the second sample chamber;
   generating an intermittent infrared radiation with the second infrared radiator;
   detecting a third intensity of infrared radiation with the third detector;
   determining at least a third concentration of a third gas as a function of a third intensity of the infrared radiation;
   detecting a fourth intensity of infrared radiation with the second filter chamber, the second filter chamber being configured as a fourth detector; and
   determining at least a fourth concentration of a fourth gas as a function of the fourth intensity of the infrared radiation.

11. The method according to claim 10, wherein a calorific value or a heating value of the fuel gas is determined as a function of the first, second, third, and/or fourth concentration.

12. The method according to claim 10, wherein a lower or upper Wobbe index of the fuel gas is determined as a function of the first, second, third, and/or fourth concentration.

13. The first detector according to claim 1, wherein the photoacoustic effect by which the first detector operates is a result of a pressure wave caused by an absorption of infrared radiation from the first infrared emitter over a time interval that generates a quantity of heat in the first detector.

14. The first detector according to claim 1, wherein the first sample chamber is connected to the fuel gas inlet for a burner so that the fuel gas for the burner flows through the first sample chamber before being provided to the burner for combustion.

* * * * *